US009063046B1

(12) United States Patent
Sagripanti

(10) Patent No.: US 9,063,046 B1
(45) Date of Patent: Jun. 23, 2015

(54) HAND-HELD DEVICE WITH REAGENTS AND METHOD FOR DETECTION AND DIAGNOSTICS

(71) Applicant: U.S. Army Edgewood Chemical and Biological Command, APG, MD (US)

(72) Inventor: Jose Luis Sagripanti, Bel Air, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 0 days.

(21) Appl. No.: 14/184,320

(22) Filed: Feb. 19, 2014

Related U.S. Application Data

(62) Division of application No. 13/445,490, filed on Apr. 12, 2012, now Pat. No. 8,658,088.

(51) Int. Cl.

| | |
|---|---|
| ***A61L 2/00*** | (2006.01) |
| ***B08B 3/00*** | (2006.01) |
| ***F04F 10/00*** | (2006.01) |
| ***A01N 1/00*** | (2006.01) |
| ***G01N 1/38*** | (2006.01) |

(52) U.S. Cl.
CPC .......................................... *G01N 1/38* (2013.01)

(58) Field of Classification Search
CPC .......... A61L 2/0017; B08B 3/04; A01N 1/02; G01N 33/53
USPC .............. 422/536, 292, 301; 134/94.1, 104.2; 435/1.1, 1.2, 32, 287.4; 137/140, 544, 137/571
See application file for complete search history.

(56) References Cited

U.S. PATENT DOCUMENTS 6,743,574 B1 * 6/2004 Wolfinbarger et al. ........ 435/1.1

* cited by examiner

*Primary Examiner* — Monzer R Chorbaji
(74) *Attorney, Agent, or Firm* — Ulysses John Biffoni

(57) ABSTRACT

A hand-held device and method of processing a biological threat agent sample such that any infectious organism is rendered harmless while preserving it for subsequent testing, the method comprising placing a sample comprising a biological threat agent in a reservoir; adding a first reagent comprising peracetic acid in sufficient concentration to reach a predetermined minimal concentration after mixing with the sample in the reservoir; inactivating the sample upon interaction of the sample with the first reagent for a predetermined period of time at a predetermined temperature; removing the inactivated sample from the reservoir; and providing the inactivated sample for subsequent diagnostic testing, wherein the subsequent diagnostic testing is unaffected by inactivation of the sample. In another embodiment, the first reagent comprises a cupric salt, which is mixed with ascorbic acid and hydrogen peroxide to generate cupric ascorbate.

8 Claims, 13 Drawing Sheets

FIG. 1: Screening experiments with disinfecting and inactivating chemicals used at the reaction time of 30 min at 21°C

| Inactivating Chemicals | Pixuna Virus | | | | Bacillus atrophaeus spores | | | |
|---|---|---|---|---|---|---|---|---|
| | T0: no Chemical | T1: reduced concentration | T2: concentration inactivation purposes | T3: increased concentration | T0: no Chemical | T1: reduced concentration | T2: concentration inactivation purposes | T3: increased concentration |
| **Peracetic acid** | 0% | 0.003% | 0.03% | 0.3% | 0% | 0.0035% | 0.03% | 0.3% |
| titer reduction ($log_{10}$) | ---- | 1 | >6 | > 6 | ---- | < 0.1 | >6 | > 6 |
| PCR detection[b] | +++ | ++ | ++ | + | ++ | ++ | ++ | ++ |
| ELISA signal[c] | +++ | +++ | – | – | +++ | +++ | +++ | +++ /++ |
| **Na-hypochorite** | 0% | 0.005% | 0.05% | 0.5% | 0% | 0.005% | 0.05% | 0.5% |
| titer reduction ($log_{10}$) | ---- | 0 | 3 | > 6 | ---- | > 3 | >6 | > 6 |
| PCR detection[b] | ++ | ++ | – | – | ++ | – | – | – |
| ELISA signal[c] | +++ | ++ | – | – | +++ | ++ | +++ | +++ |
| **Cupric ascorbate** | 0% | 0.1 % Cu[a,g] | 0.5 % Cu[a,g] | 2.5 % Cu[a,g] | 0% | 0.1 % Cu[a] | 0.5 % Cu[a] | 2.5 % Cu[a] |
| titer reduction ($log_{10}$) | ---- | > 4 | > 6 | > 6 | ---- | < 1 | > 6 | > 6 |
| PCR detection[b] | +++ | ++ | ++ | + | ++ | ++ | ++ | – |
| ELISA signal[c] | +++ | + | – | – | +++ | +++ | +++ | +++ |
| **Glutaraldehyde[f]** | 0% | 0.4% | 2% | 4% | 0% | 0.4% | 2% | 4% |
| titer reduction ($log_{10}$) | ---- | > 6 | nd[e] | nd[e] | ---- | > 2 | > 2 | > 6 |
| PCR detection[b] | ++ | – | – | – | ++ | ++ | ++ | ++ |
| ELISA signal[c] | +++ | – | – | – | +++ | +++ | +++ | +++ |
| **Formaldehyde** | 0% | 4% | 8% | 16% | 0% | 4% | 8% | 16% |
| titer reduction ($log_{10}$) | ---- | > 6 | toxic | toxic | ---- | < 0.1 | < 0.1 | > 1 |
| PCR detection[b] | ++ | – | – | – | ++ | ++ | + | – |
| ELISA signal[c] | +++ | ++ | + | – | +++ | ++ | ++ | + |
| **Hydrogen peroxide** | 0% | 1% | 10% | 15% | 0% | 1% | 10% | 15% |
| titer reduction ($log_{10}$) | ---- | < 1 | 3 | > 6 | ---- | < 0.1 | < 0.1 | 1 |
| PCR detection[b] | ++ | ++ | + | – | ++ | ++ | ++ | ++ |
| ELISA signal[c] | +++ | +++ | + | – | +++ | +++ | +++ | +++ |
| **Guadinium-ISCN[d]** | 0 M | 0.035 M | 0.35 M | 3.5 M | 0 M | 0.035 M | 0.35 M | 3.5 M |
| titer reduction ($log_{10}$) | ---- | 0 | 0 | > 5 | ---- | < 0.5 | < 0.5 | < 0.5 |
| PCR detection[b] | ++ | ++ | ++ | ++ | ++ | ++ | ++ | ++ |
| ELISA signal[c] | +++ | +++ | ++ | + | +++ | +++ | +++ | + |

[a] Cupric ascorbate concentrations: T1: 0.1 % Cu, 0.02% AscH, 0.0006% H2O2, T2: 0.5% Cu, 0.1 % AscH, 0.003% H2O2, T3: 2.5% Cu, 0.5% AscH, 0.015% H2O2

[b] PCR (cycles): +++ < 25, ++ <30, + < 35, - >35

[c] ELISA OD450 (% recovery): +++ >75, ++ >50, + >25, - <25

[d] Guadinium- Isothiocyanate

[e] nd: not determined

[f] The inactivation of PIXV by glutaraldehyde was indetermined due to toxicity to the cultured mammalian cells.

[g] The toxicity of cupric ascorbate on ELISA assays was avoided by previous treatment of samples with 100 mM EDTA.

Shaded concentration generally used for liquid sterilization

Effect of PAA treatment on ELISA inactivation of >6 log$_{10}$ x-axis: PAA conc. (% w/v)
y-axis: relative OD 450 nm (%)

Legend: ····•···· Spores ···◦··· P. aeruginosa ---■--- PIXV —□— VACV

HAND-HELD DEVICE WITH REAGENTS AND METHOD FOR DETECTION AND DIAGNOSTICS

CROSS-REFERENCE TO RELATED APPLICATIONS

This application is a divisional of application Ser. No. 13/445,490 filed on Apr. 12, 2012, now U.S. Pat. No. 8,658,088, which is commonly assigned.

CROSS REFERENCE TO RELATED APPLICATION

This application claims the benefit of U.S. Provisional Patent Application No. 61/494,118 filed on Jun. 7, 2011, the contents of which, in its entirety, is herein incorporated by reference.

GOVERNMENT INTEREST

The embodiments herein may be manufactured, used, and/or licensed by or for the United States Government without the payment of royalties thereon.

BACKGROUND

1. Technical Field

The embodiments herein generally relate to diagnostic devices and methods, and, more particularly, to a hand-held device with reagents and methods for rendering safe-to-handle samples with infectious agents while preserving bacterial and viral signatures for immune and genetic-based detection diagnostics and forensics.

2. Description of the Related Art

The high risk associated with biological threat agents determines that any suspicious sample be handled under strict surety and safety controls and processed under high level containment in specialized laboratories. These specialized facilities are complex, very expensive to operate, and need to be staffed by personnel from an extremely limited pool of experts. In addition, safe means of transporting samples suspected of containing highly virulent agents to specialized high level containment laboratories for analysis is also expensive, requiring in many countries the custody of armed personnel. It can be estimated that several million dollars are spent annually worldwide to secure and safely transport an ever-increasing stream of suspicious biological samples which are collected in theatres of war, as well as in domestic environments.

As an example, U.S. Pat. No. 7,851,207 issued on Dec. 14, 2010, the complete disclosure of which, in its entirety, is herein incorporated by reference describes a device used to identify a variety of microbial agents simultaneously. The '207 patent is advantageous for the purposes for which it was developed. The sample agents that are tested are generally not preserved for subsequent detection, diagnostics, or forensics. Moreover, the '207 patent provides denaturation and purification steps that prevent immune-based testing. However, while the '207 patent analyses the sample using a single and specific nucleic-acid based methodology (hybridization), it does not preserve the sample for future testing. Accordingly, there remains a need for diagnostic techniques that reserve potentially dangerous samples for future immune or various nucleic acid based testing.

SUMMARY

In view of the foregoing, an embodiment herein provides a method of processing a biological threat agent sample such that any infectious organism is rendered harmless while preserving it for subsequent testing, the method comprising placing a sample comprising a biological threat agent in a reservoir; adding a first reagent comprising peracetic acid in sufficient concentration to reach a predetermined minimal concentration after mixing with the sample in the reservoir; inactivating the sample upon interaction of the sample with the first reagent for a predetermined period of time at a predetermined temperature; removing the inactivated sample from the reservoir; and providing the inactivated sample for subsequent diagnostic testing, wherein the subsequent diagnostic testing is unaffected by inactivation of the sample. Peracetic acid in the reservoir should be in sufficient concentration so as to reach, after mixing with the sample, a minimal concentration of 0.03% v/v. For example a tested effective mixture includes placing peracetic acid of 0.06% v/v in the reservoir to which an equal volume of the sample is added, resulting in an active final concentration of 0.03% v/v. The sample and the first reagent may be placed in the reservoir for approximately 30 minutes at approximately 21° C. The method may further comprise adding a second reagent comprising any of diluents and catalase in the reservoir to decompose any remaining peracetic acid after inactivation. The subsequent diagnostic testing may comprise any of a polymerase chain reaction test and an enzyme linked immunoassays test. The peracetic acid preferably comprises 0.03% peracetic acid as a final active concentration after diluting with the sample.

Another embodiment provides a method of processing biological threat agents, the method comprising placing a sample comprising a biological threat agent in a reservoir comprising a first reagent comprising a cupric salt such as chloride or sulfate; generating in situ cupric ascorbate by adding to the reservoir a second reagent comprising ascorbic acid and an amount of hydrogen peroxide that is in sufficient quantity to assure oxygenation of the mixture; inactivating the sample upon interaction of the sample with the cupric ascorbate mixture for a predetermined period of time at a predetermined temperature; removing the inactivated sample from the reservoir; and providing the inactivated sample for subsequent diagnostic testing, wherein the subsequent diagnostic testing is unaffected by inactivation of the sample. The sample with the first reagent and second reagent may be left in the reservoir for approximately 30 minutes at approximately 21° C. The subsequent diagnostic testing may comprise any of a polymerase chain reaction test, nucleic acid hybridization or other nucleic acid-based tests and an enzyme linked immunoassay, immunoprecipitation, and any other immuno-based test. Moreover, the cupric salt may comprise cupric chloride. The first reagent may comprise a cupric salt in sufficient concentration so as to result in a final concentration of 0.5% w/v in cupric ions after dilution with the sample and the second reagent. The concentration of ascorbic acid should provide a final concentration such that mixing the sample and first reagent results in 0.1% w/v ascorbate and a small amount of hydrogen peroxide to assure aerobiosis (presence of oxygen) in a final concentration after mixing with all others of 0.003% v/vt. For example, a tested mixture resulting in concentrations with adequate potency comprising 5 volumes of cupric chloride 2% w/v in cupric ions in a first reservoir of the device, and in a second reservoir, 4 volumes of ascorbic acid 0.5% w/v with 1 volume of hydrogen peroxide 0.06% v/v. At the time of use, 10 volumes of sample are added to the device and all components are mixed together. The mixture indicated above results in final concentrations of 0.5% w/v cupric ions, 0.1% w/v ascorbate, and 0.003% v/v peroxide. The method may further comprise adding ethylenediaminetetraacetic acid to the inactivated sample. Peracetic acid is the only biocidal reagent while cupric ascorbate inactivation employs two reagents mixed in situ.

Another embodiment provides a hand-held device for sample preparation of samples suspected of containing biological threat agents, the device comprising a reservoir that holds a sample comprising a biological threat agent; a first dispensing unit operatively connected to the reservoir, wherein the first dispensing unit adds a first reagent comprising peracetic acid in sufficient concentration to reach a predetermined minimal concentration after mixing with the sample in the reservoir, wherein the sample becomes inactivated upon interaction of the sample with the first reagent for a predetermined period of time at a predetermined temperature; and a filter operatively connected to the reservoir and the first dispensing unit, wherein the filter removes the inactivated sample from the reservoir, wherein the inactivated sample is capable for subsequent diagnostic testing, and wherein the subsequent diagnostic testing is unaffected by inactivation of the sample. The sample and the first reagent may be placed in the reservoir for approximately 30 minutes at approximately 21° C. The device may further comprise a second dispensing unit operatively connected to the reservoir, wherein the second dispensing unit adds a second reagent comprising any of diluents, catalase and a mixture of ascorbic acid and hydrogen peroxide into the reservoir. In the peracetic acid based method, the peracetic acid preferably comprises 0.03% peracetic acid. In the cupric ascorbate based method, the cupric salt may comprise cupric chloride as the first reagent, and the second reagent may comprise ascorbic acid and a small amount of hydrogen peroxide to provide, after mixing with the sample, the final concentrations described above.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 1 is a table illustrating screening experiments with disinfecting and inactivating chemicals according to an embodiment herein;

DETAILED DESCRIPTION

Figure 2A:
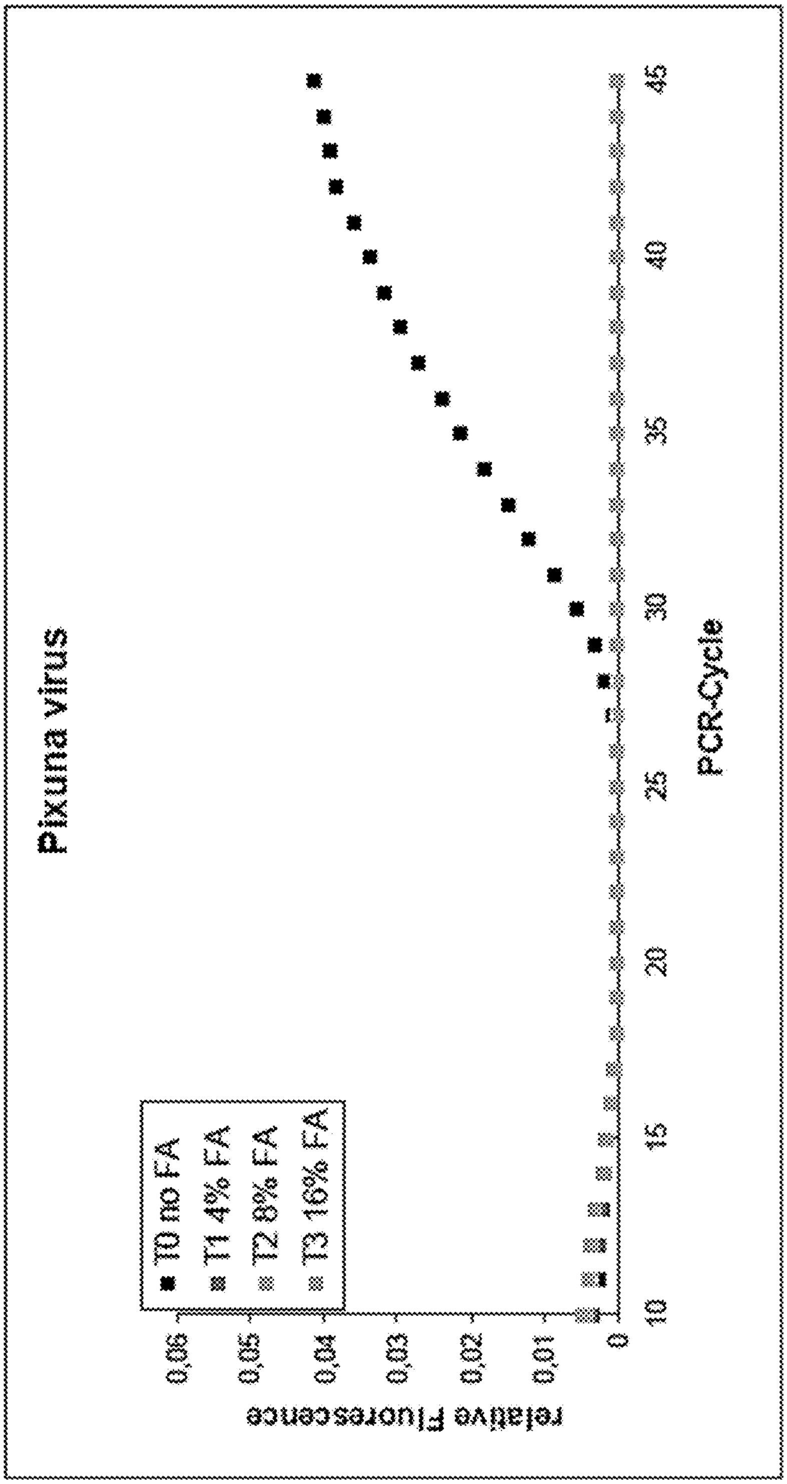
FIGS. 2A through 2D are graphical representations illustrating the deleterious effect of selected germicidal agents on PCR assays according to an embodiment herein.
Figure 2B:
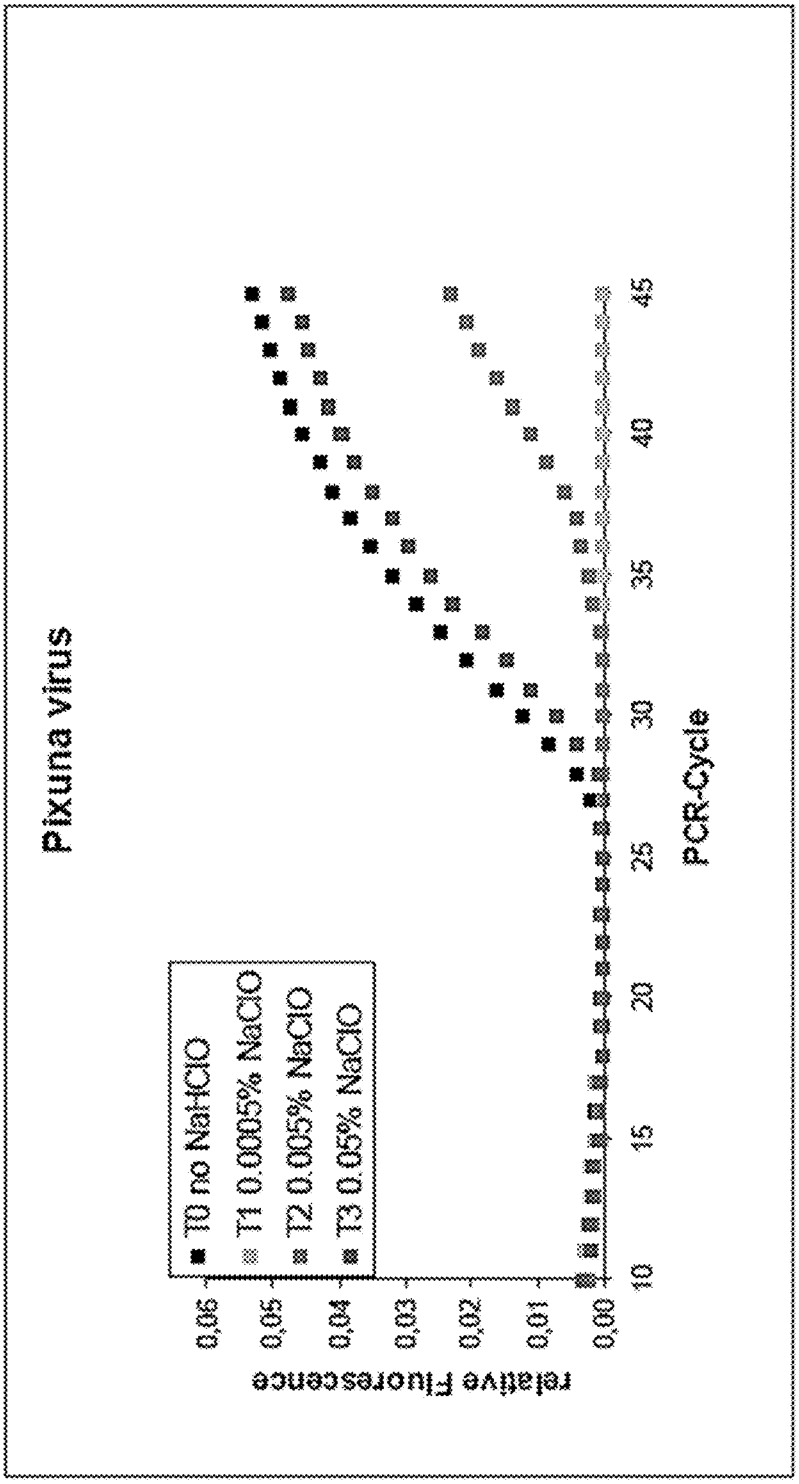
Figure 2C:
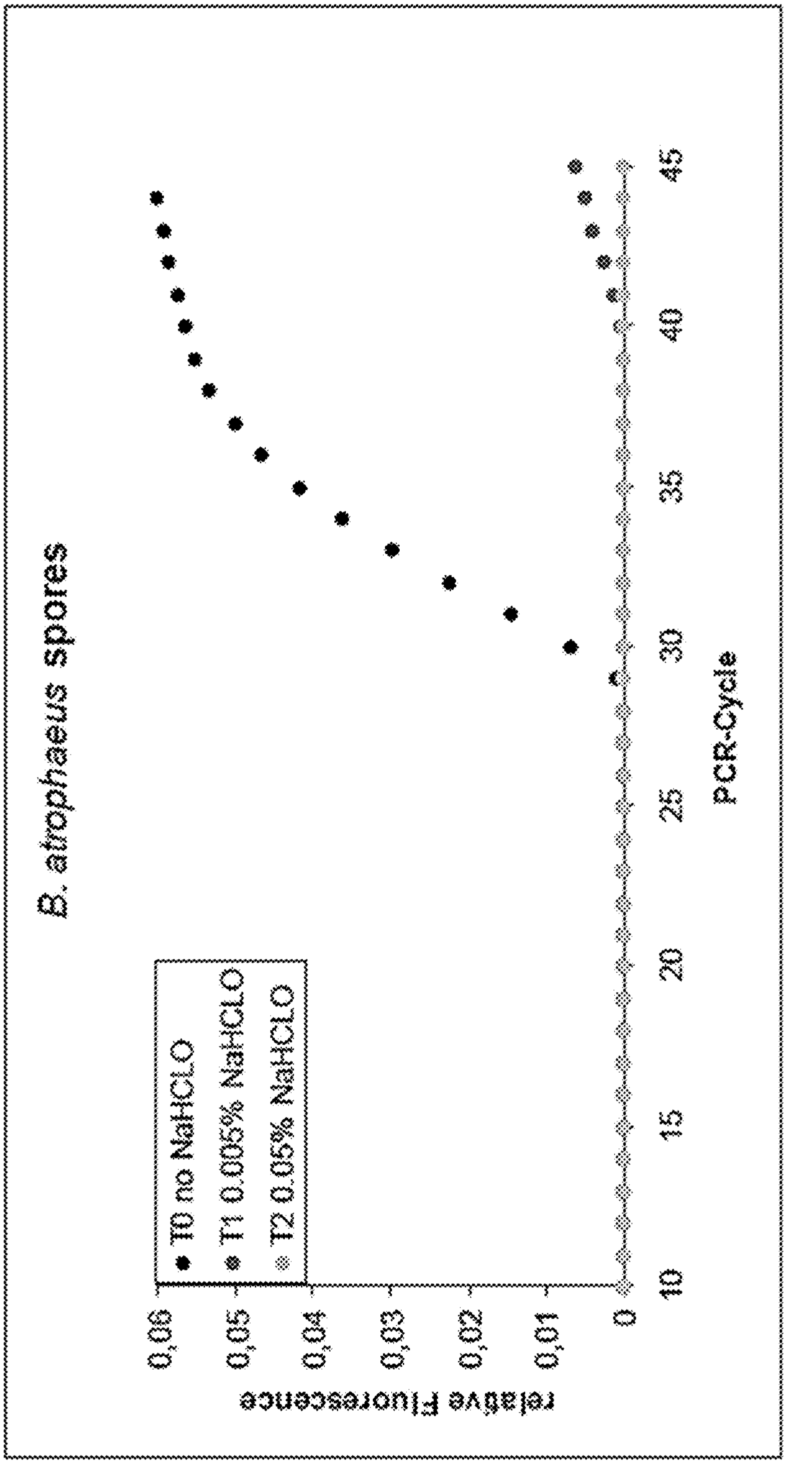

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein provide a cost-effective method for specific microbicidal chemistry and associated hardware including a hand-held device to rapidly inactivate high-threat biological agents in suspected samples, without hindering subsequent identification. Accordingly, the embodiments herein allow for a significant cost savings of the several million dollars currently spent annually to secure and safely transport an ever-increasing stream of suspicious samples suspected to contain virulent agents which are collected in military and non-military settings both domestically and internationally. Referring now to the drawings, and more particularly to FIGS. 1 through 6B, where similar reference characters denote corresponding features consistently throughout the figures, there are shown preferred embodiments.

The embodiments herein provide unique chemical compositions that can completely kill all organisms being tested while preserving the performance of detection and diagnostic methods. Experimental testing is performed on the effect of a wide variety of microbicidal agents on: (a) the survival of vegetative bacteria, bacterial spores, DNA viruses and RNA viruses; (b) the performance of DNA-based detection and diagnostic methods; and (c) the performance of immune-based detection and diagnostic methods in order to develop the aforementioned chemical compositions.

Considerable knowledge has been accumulated regarding the efficiency of microbicidal reagents and methods, particularly on inactivating bacterial spores in liquids, on surfaces, or in aerosols but the subsequent deleterious effect of these disinfectants on the performance of either nucleic-acid or immune-based diagnostics precluded their use for processing of suspected field samples. As a result, the embodiments herein include experimental testing of two aldehydes (formaldehyde and glutaraldehyde), a halogenating agent (hypochlorite), two peroxides (hydrogen peroxide and peracetic acid), and a free radical damaging agent (cupric ascorbate). In addition, the experimental testing included a chaotropic agent, guanidium thiocyanate, with the well-established ability to dissociate biological structures and liberate intact nucleic acids for analysis. Spores of *Bacillus* (*B.*) *atrophaeus* are selected as an example microbial target because these have been frequently used in sporicidal studies and also because spores of *B. atrophaeus* show similar sensitivity to chemical germicides than virulent strains of *B. anthracis*. Cells of *Pseudomonas* (*P.*) *aeruginosa* are selected for testing because this bacterium is in the group with the highest resistance to disinfection among the vegetative cells of bacteria frequently causing human infection in hospitals.

To assess the effect of disinfectants on viruses, mainly on the potential hindrance on virus detection, the Vaccinia virus (VACV) is included in the experimental testing, which is an orthopoxvirus (with DNA genome) generally used as a surrogate for the Smallpox virus, and Pixuna virus (PIXV), which is an alphavirus that has been used as a simulant or surrogate for the Venezuelan equine encephalitis virus and other highly pathogenic RNA viruses. The inactivation of all these microorganisms is followed for more than 6 $\log_{10}$, since this is the standard assurance level generally accepted for safety of medical devices and contaminated environments (based on the American ASTM Standard E-2414-05). The effect of germicidal agents is studied on the performance of polymerase chain reaction (PCR) tests as it is one of the most frequently used nucleic acid-based diagnostic methods and an enzyme linked immunoassays (ELISA), which is one of the most widely used immunedetection methods.

The embodiments herein provide for the screening of chemical methods that completely inactivate pathogens with minimal impairment of diagnostics. The concentrations generally employed for chemical disinfection and sterilization of microbial pathogens correspond to hypochlorite 0.05% v/v (volume/volume; volume concentration), glutaraldehyde 2% v/v, peracetic acid 0.03% v/v, formaldehyde 8% v/v, hydrogen peroxide 10%, and cupric ascorbate at 0.5% in cupric ions w/v (mass/volume; mass concentration). Bacterial spores and viruses are exposed to the different chemical germicides at the following concentrations: hypochlorite 0.05% v/v, glutaraldehyde 2% v/v, peracetic acid 0.03% v/v, formaldehyde 8% v/v, hydrogen peroxide 10%, and cupric ascorbate at 0.5% in cupric ions w/v, as well as to one lower (generally one-tenth) and one higher (generally 10-fold) concentration.

In addition to commonly used germicides, the effect of guanidium thiocyanate, which is known to disrupt cells and liberate nucleic acids without damaging them is also included in the experimental testing. One requirement for selection of disinfecting agents is the complete, fast, and reliable inactivation of spores at or near room temperature since any method to be developed should be rapid and fieldable. The results of these exploratory experiments with common disinfecting and inactivating chemicals are summarized in FIG. 1. The efficiency of the reagents is rated not only for their reduction of infectivity, but also for their preservation of immunological reactivity and nucleic acid detection.

As demonstrated by the data in FIG. 1, some chemical germicides such as hydrogen peroxide, formaldehyde, and glutaraldehyde did not completely kill all of the spores challenged in testing. These same chemicals at their concentration of use also impair the performance of PCR and ELISA tests to detect spores and viruses as illustrated in FIG. 1.

This impairing effect on PCR and ELISA is more pronounced on viruses than on spores (for example, see FIGS. 2A through 2D). FIGS. 2A through 2D are graphical representations illustrating the deleterious effect of selected germicidal agents on PCR assays according to an embodiment herein. More particularly, FIGS. 2A through 2D depict the deleterious effects of different concentrations of formaldehyde and sodium hypochloride treatment at a reaction time of 30 min at 21° C. on PIXV and *B. atrophaeus* spores PCR analysis in comparison to untreated controls. Microbes are treated with either water as a non-microbicidal control (To) or with Formaldehyde (FA) or sodium hypochlorite (NaClO) at the concentrations indicated inside the legend boxes in FIGS. 2A through 2D. The PCR proceeded as described further below in the listing of materials and methods and the relative fluorescence as a function of number of amplification cycles is shown for PIXV (in FIGS. 2A and 2B) or for spores of *B. atrophaeus* (in FIGS. 2C and 2D).

Figure 2D:
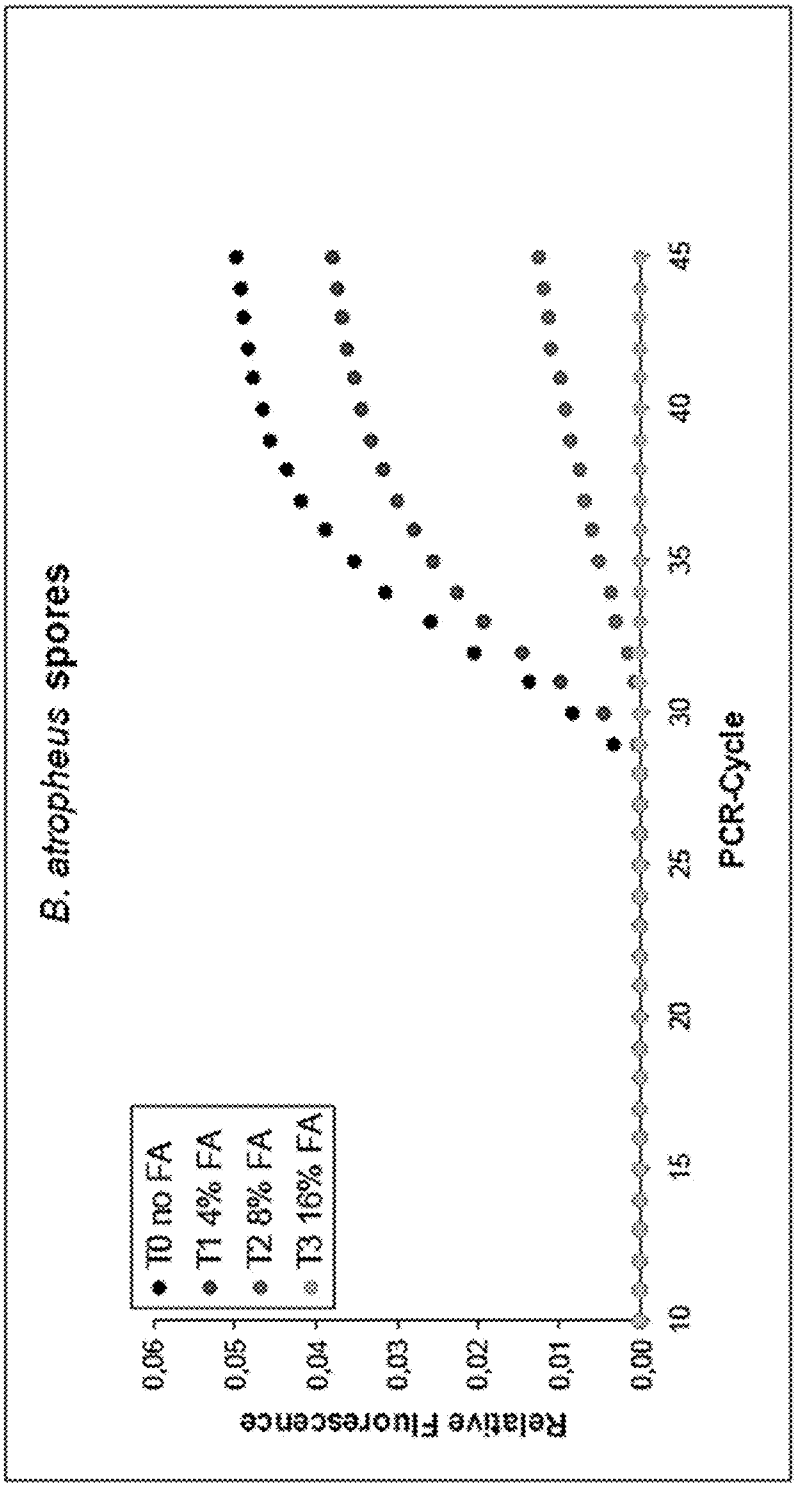

Formaldehyde 8% decreases the relative fluorescence of PCR testing of spores but has only a minimal effect on their Ct-value (see FIG. 2D). In contrast, sodium hypochlorite at the concentration generally used in liquid sterilization (0.05% v/v) completely inhibits PCR assays of spores and viruses (see FIGS. 2B and 2C) as well as the ELISA of PIXV. Guanidium thiocyanate at 3.5 M, close to its maximal aqueous solubility, does not hinder PCR or ELISA but has little inactivating effect on spores and PIXV (see FIG. 1). Incubation at room temperature (21° C.) with either 0.5% cupric ascorbate or with 0.03% peracetic acid reduces spores and virus titer by at least 6 $\log_{10}$ hindering diagnostic performance of PCR and ELISA slightly except that for PIXV the preliminary ELISA results are negative.

The embodiments herein provide for selected chemical inactivation methods suitable for subsequent diagnostics. The results from the agent screening shown in FIG. I clearly indicates peracetic acid and cupric ascorbate as the two most promising chemical inactivating reagents for development of a fieldable inactivating method that will not impair subsequent diagnostics. For further and more detailed studies VACV is also included as a surrogate for the Smallpox virus and vegetative cells from *P. aeruginosa* as a bacterium with relatively high resistance to disinfection. Peracetic acid, which at 0.03% v/v kills beyond detection levels spores>6 $\log_{10}$ and PIXV (>7 $\log_{10}$), affects the corresponding PCR and ELISA assays differently as shown in FIGS. 3A and 3B.

Figure 3A:
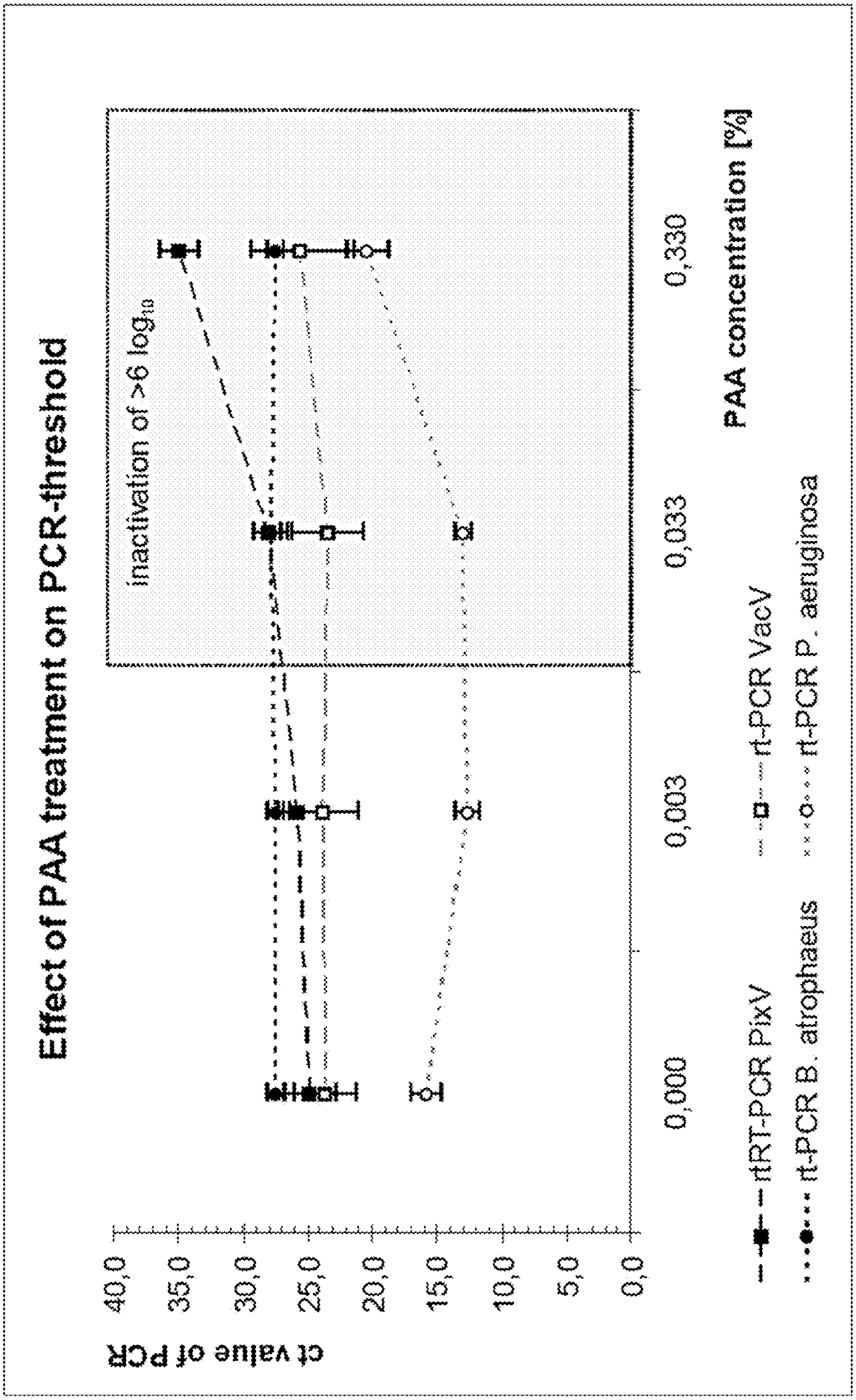
FIGS. 3A and 3B are graphical representations illustrating the effect of peracetic acid on PCR and ELISA according to an embodiment herein.
Figure 3B:
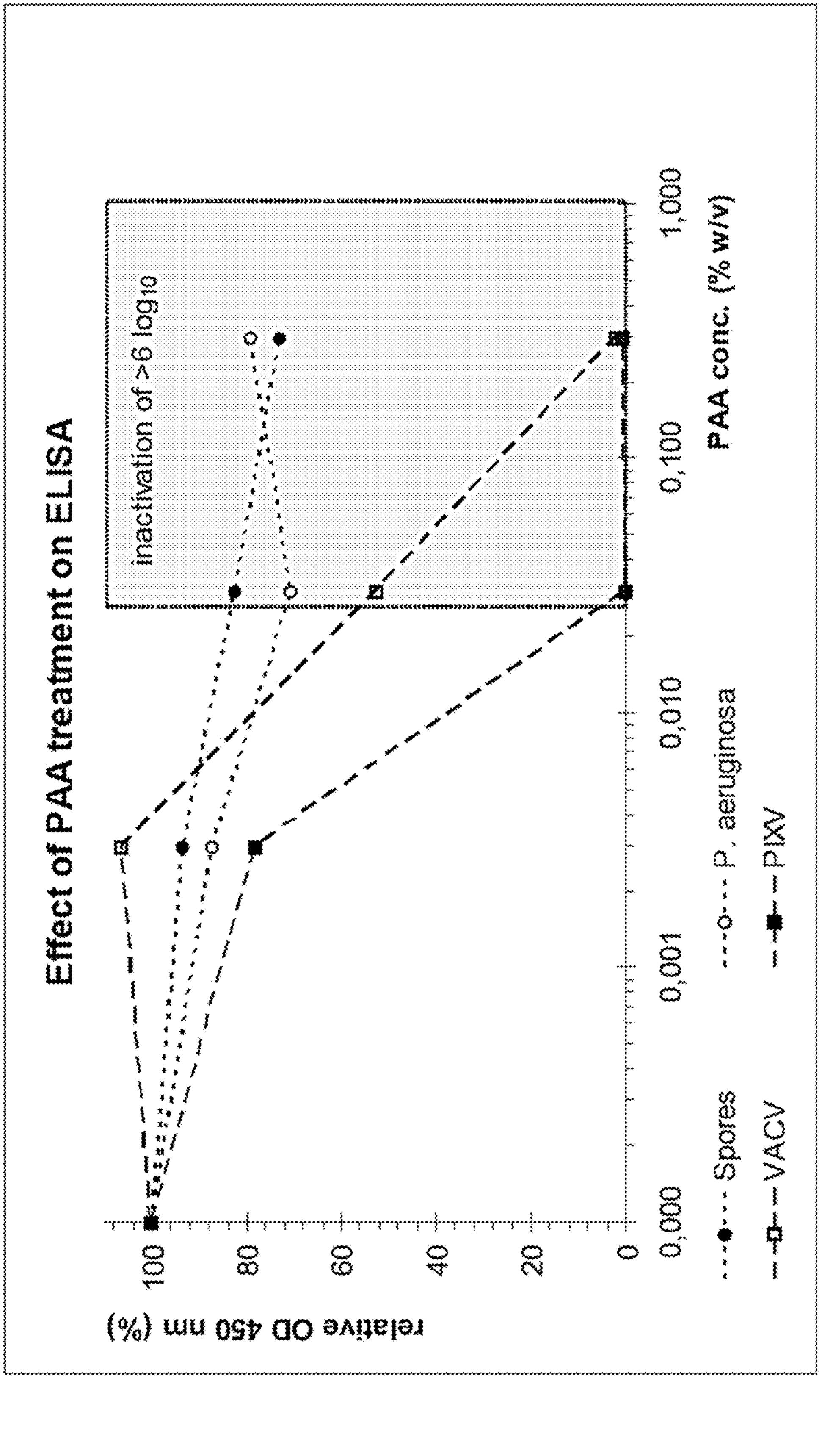

FIGS. 3A and 3B are graphical representations illustrating the effect of peracetic acid on PCR and ELISA according to the embodiments herein. All microorganisms are treated with PAA at concentrations of 0.003%, 0.03%, and 0.3%. The graph in FIG. 3A shows the effect of PAA treatment on the Ct values of PCR analysis of *B. atrophaeus* spores (full circles), *P. aeruginosa* (open circles), PIXV (full squares), and VACV (open squares) relative to untreated controls. The Ct value of untreated controls are 27.5±0.58 SD for *B. atrophaeus*, 15.8±1.16 SD for *P. aeruginosa,* 24.7±2.0 SD for PIXV, and 23.6±2.7 SD for VACV. FIG. 3B depicts the effect of the same treatment with peracetic acid on the corresponding ELISA. In FIGS. 3A and 3B, the range of inactivation of >6 $\log_{10}$ is indicated as a shaded area.

For both spores and viruses, PCR sensitivity is only marginally affected (see FIG. 3A), and the immunoassay of viruses are completely inhibited as the inactivating concentrations (see FIG. 3B). The ELISA signal results obtained for spores (see FIG. 3B) are only affected by PAA at a concentration ten times higher than the concentration providing high microbicidal efficacy (0.03%, FIGS. 2A through 2D) and are generally used.

Figure 4A:
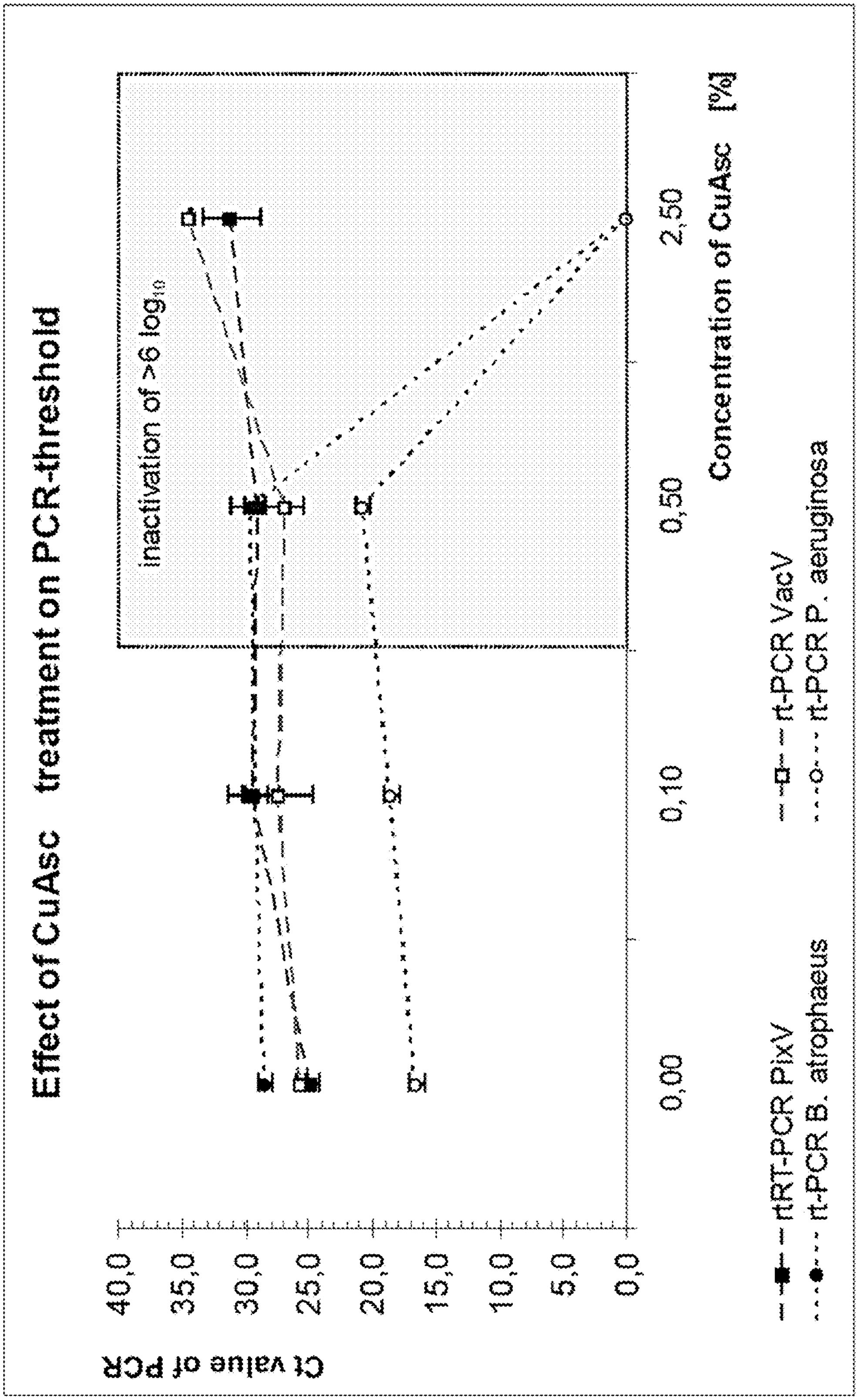
FIGS. 4A and 4B are graphical representations illustrating the effect of cupric ascorbate on PCR and ELISA according to an embodiment herein.
Figure 4B:
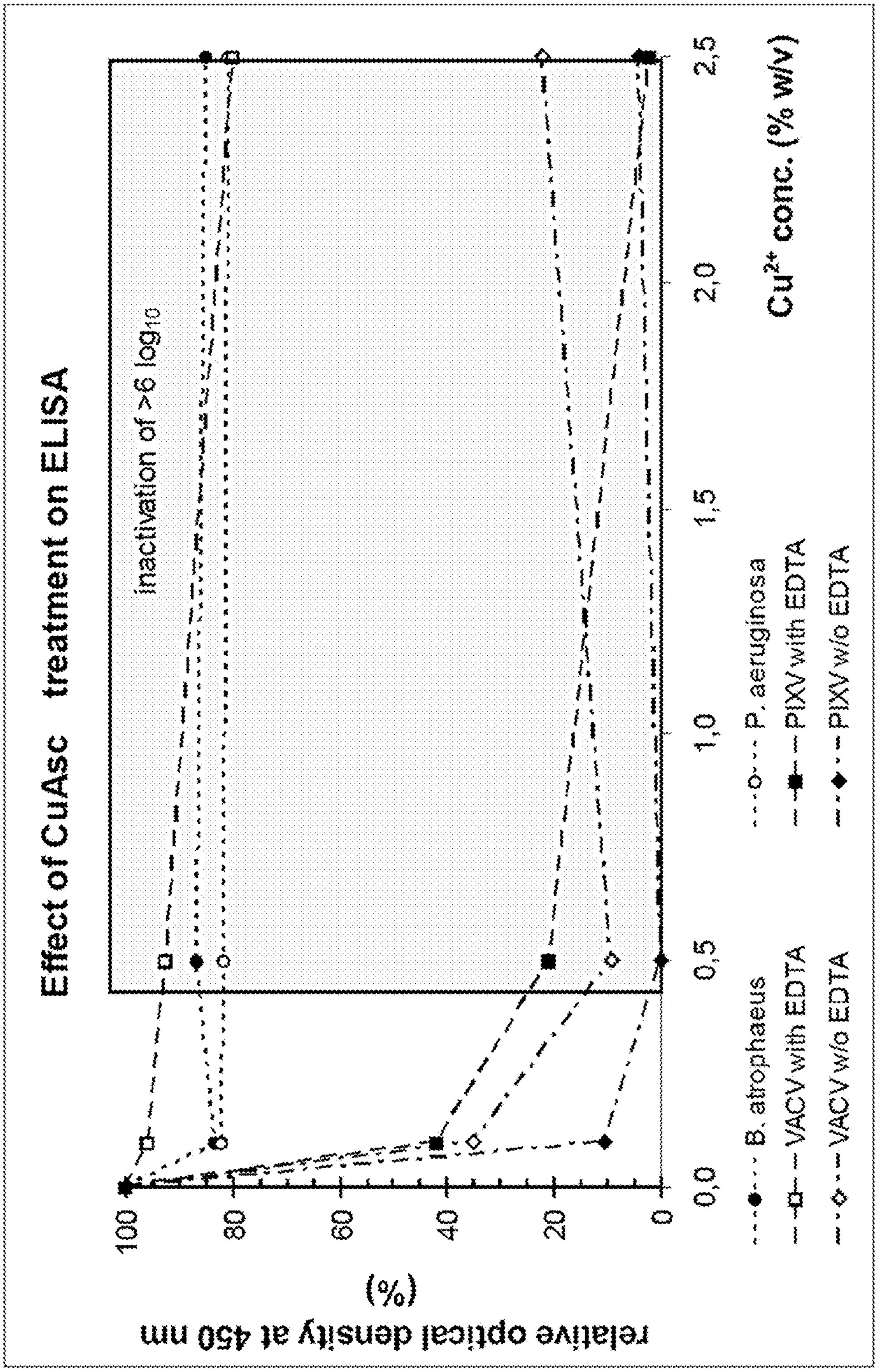

FIGS. 4A and 4B are graphical representations illustrating the effect of cupric ascorbate on PCR and ELISA according to the embodiments herein. All microbes are treated with three CuAsc concentrations of 0.1%, 0.5%, and 2.5% (in cupric ions). The range of inactivation of >6 log 10 is indicated in FIGS. 4A and 4B. The graph in FIG. 4A shows the effect of treatment with different levels of CuAsc on PCR and RT-PCR. FIG. 4A also indicates the Ct values obtained by PCR analysis of *B. atrophaeus* spores (full circles), *P. aeruginosa* (open circles), PIXV (full squares), and VACV (open squares). The Ct values obtained for the untreated controls are 28.5±0.58 SD for spores, 16.5±0.58 SD for *P. aeruginosa,* 24.9±0.9 SD for PIXV, and 25.6±0.4 SD for VACV. FIG. 4B further depicts the effect of cupric ascorbate on the same viruses without chelation or after chelation of Cu++ with 100 mM ethylenediaminetetraacetic acid (EDTA) on ELISA. In FIGS. 4A and 4B, the range of inactivation of >6 log 10 is indicated as a shaded area.

Accordingly, the effect of cupric ascorbate at a concentration of 0.5% in Cu++ ions on PCR and ELISA assays is presented in FIGS. 4A and 4B, showing that the impact of disinfection on PCR assay of spores or viruses is neglectable. At a five-fold higher concentration than generally recommended for liquid sterilization, the PCR signal is lost for PIXV and VACV but does not impair PCR of spores or *P. aeruginosa.*

The data presented in FIGS. 3A through 4B indicate that peracetic acid and cupric ascorbate increase the number of PCR cycles (relative to the number of cycles in the controls not exposed to germicidal agent) to detect PIXV and VACV by about 4 cycles and 0 cycles, respectively. FIGS. 3A through 4B also demonstrate that no change is observed in the number of PCR cycles to detect spores or vegetative bacteria (between 0 and 1 cycle respectively) after inactivation with either peracetic acid or cupric ascorbate.

The limit of detection of ELISA tests to determine spores is marginally reduced after treatment with peracetic acid or with cupric ascorbate. In contrast, using ELISA to detect viruses is sensitive to disinfection (see FIG. 3B). Several substances are included in the experiments in an attempt to minimize the impairing effect of peracetic acid and cupric ascorbate on viral ELISA. The addition to post disinfection mixes of catalase (32 to 320 units) or of Tris-EDTA, pH 8, in order to degrade the remaining peroxide radicals in peracetic acid or neutralize acid cannot restore the PIXV ELISA signal after disinfection with peracetic acid. Among all the substances under testing, EDTA best prevents the impairment of viral ELISAs by disinfection with cupric ascorbate. The results shown in FIG. 4B indicates that cupric ascorbate without post-treatment with EDTA completely inhibits immunological reactions with the PIXV and the VACV. However, the addition of EDTA, pH 8, up to a final concentration of 100 mM after the disinfection with cupric ascorbate protects the ELISA signal from VACV (a virus whose genome is DNA) to about 90% compared to the untreated sample. Immunoassays to detect PIXV (a virus with RNA genome) are more sensitive to cupric ascorbate since EDTA retains only about 20% of the signal compared to the untreated antigen. These results suggest that viral PIXV antigens are more sensitive to oxidation and inactivation by cupric ascorbate than VACV antigens.

Peracetic acid reduces the sensitivity of spores immunoassays to nearly 20% of the results obtained with untreated controls, while cupric ascorbate has no impact on these assays. Moreover, inactivation of vegetative bacteria, bacterial spores, or viruses with these reagents does not lead to false-positive signals in subsequent PCR or ELISA testing.

Figure 5A:
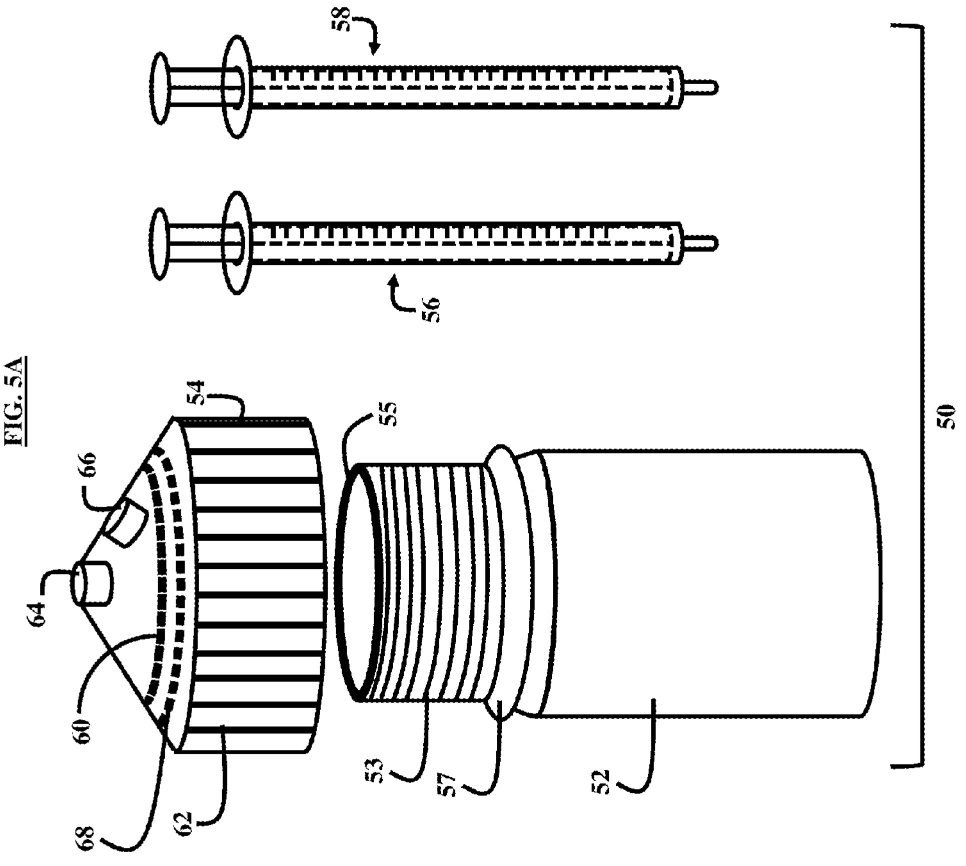
FIGS. 5A and 5B illustrate a hand-held device according to an embodiment herein.
Figure 5B:
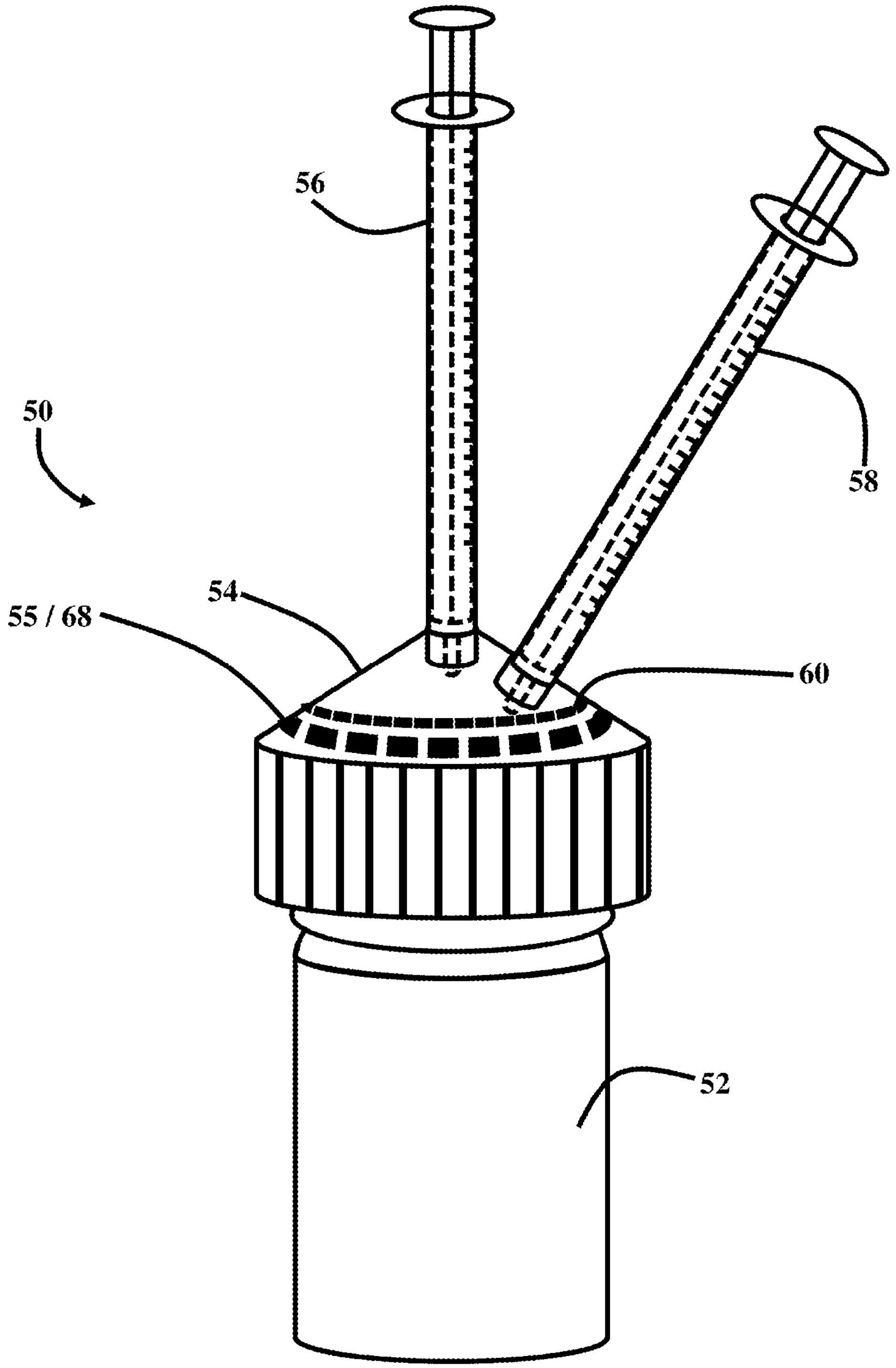

As shown in FIGS. 5A and 5B, with respect to FIGS. 1 through 4B, the embodiments herein further include a handheld device 50 to inactivate microbes in suspected samples without hindering subsequent diagnostics or detection. The device 50 is dimensioned and configured to accommodate one or more of the reagents described above. The device 50 includes a sample reservoir 52 (for example, a jar or bottle with or without a rib 57, etc.) where the sample is resuspended or diluted in saline, and a head unit 54 which operatively connects to two dispensing mechanisms 56, 58 (for example, syringes) for dispensing reagents. The head unit 54 further includes a filter 60, gripping ribs 62, a pair of conduits 64, 66, and seal 68. The reservoir 52 may include threads 53 to engage with corresponding threads (not shown) of the head unit 54 to create a connection between the reservoir 52 and head unit 54. A corresponding seal 55 may be included on the reservoir 52, which may align with the seal 68 of the head unit 54 to create a liquid-tight connection between the reservoir 52 and head unit 54. The gripping ribs 62 allow a user to rotate the head unit 54 to open/close the device 50.

In a first embodiment, using peracetic acid as described above, one of the dispensing mechanisms 56 (for example) contains peracetic acid and the other dispensing mechanism 58 (for example) can contain diluents, catalase, or left empty. The sample is introduced in the reservoir 52 and mixed with saline, for example. Dispensing mechanism 56 with peracetic acid is emptied into reservoir 52 via conduit 64 and is left for approximately 30 minutes at room temperature. Afterwards, discharging dispensing mechanism 58 (via conduit 66) with catalase is optional depending on the type of subsequent analysis/diagnostics to be performed. The device 50 is then inverted and the inactivated sample is aspirated through the filter 60 and into dispensing mechanism 58 (via conduit 66). Dispensing mechanism 58 with the inactivated and filtered organisms is removed from the device 50 and subjected to further analysis/diagnostics under low containment requirements.

In a second embodiment, cupric chloride or other cupric salt is in dispensing mechanism 56 and a proper mixture of ascorbic acid and low amounts of hydrogen peroxide are in dispensing mechanism 58. Operation of the device 50 is the same as described in the first embodiment with the subsequent addition of the treated samples to EDTA used as a preservative.

Seven commonly used liquid disinfectants are experimentally tested in accordance with the embodiments herein. The majority of these substances either partially inactivates the microbial load or severely impairs subsequent PCR and ELISA tests. The embodiments herein provide a rapid, reliable, and straightforward method for the complete inactivation of a wide range of pathogens including spores, vegetative bacteria, and viruses, while preserving microbial nucleic acid fragments suitable for PCR reactions and proteinaceous epitopes for the detection of immunoassays. The experimental data demonstrates that a high level inactivation (more than 6 $\log_{10}$) of vegetative bacteria, bacterial spores, and DNA or RNA-viruses can be attained within approximately 30 minutes at 21° C. with either peracetic acid (0.03%) or cupric ascorbate (0.5% in Cu++) treatment with only minimal hindrance in the subsequent performance of PCR.

Although sensitivity of immunoassays depends on the affinity and concentration of available antibodies, the numerous ELISA that are experimentally performed with diverse liquid disinfectants and various microbes provide support to the conclusion that, in general, PCR assays withstand treatment with a variety of disinfectants better than immunoassays.

Peracetic acid disinfection maintains ELISA sensitivity from 84% to 90% of that of untreated controls during the detection of spores and vegetative bacteria, nearly 50% for detection of VACV, and completely inhibited ELISA detection of PIXV.

Disinfection with cupric ascorbate preserves the sensitivity of ELISA for vegetative bacteria and bacterial spores (within 80-90% of untreated controls) but without further treatment impairs the results of viral immunoassays. The addition of EDTA after incubation with cupric ascorbate preserves the signal in ELISA to detect VACV at nearly 90% of that in untreated controls and at 20% of the signal obtained with PIXV. Inactivation does not lead to false-positive signals. These signal levels are adequate for environmental detection and identification of environmental samples.

The relatively rapid inactivation of the high microbial loads in the experimental samples at room temperature by cupric ascorbate or peracetic acid used as described herein are effective means of quickly rendering field samples suspected of containing infectious agents safe for further analysis under lower containment, and at considerably lower costs. Moreover, sample disinfection with peracetic acid is simple and can be used before shipping suspected samples to those laboratories relying exclusively on PCR methods for the rapid detection of hazardous infectious agents. However, decontamination with peracetic acid should be selected only if certain that immunoassays will never be performed on the disinfected samples since the inhibition of immunoassays by peracetic acid is considerable.

Although an additional step involving the addition of EDTA is used to preserve immunodiagnostic performance, the relatively rapid and complete inactivation of all tested microbes at room temperature by cupric ascorbate appears as the most promising method to render field samples non-infectious and thus easily and safely transportable for subsequent analysis and diagnostics by PCR and/or immunodiagnostics. Some loss in immune reactivity for viruses should be expected during disinfection of samples with either cupric ascorbate or peracetic acid, but this result should be more than compensated by the concomitant gains in surety, safety, and economy resulting from handling samples as non-infectious and thus, at a much lower containment level.

The experimental materials and methods used in accordance with the embodiments herein are described below. The listed materials and methods are examples only, and the embodiments herein are not limited to these particular materials and methods.

Microbial species and sources: *Bacillus atrophaeus* (strain ATCC 9372) is obtained from the American Type Culture Collection (USA). Spores of *B. atrophaeus* are prepared in accordance with the DIN EN 14347 (EN 14347, 2005. Chemical disinfectants and antiseptics. Basic sporicidal activity. Test method and requirements; phase 1, step 1) and resuspended at a concentration of $2\times10^{8}$ spores per mL. *P. aeruginosa* (strain DSm 1253) is obtained from the German strain culture collection (Deutsche Sammlung von Mikroorganismen und Zellkulturen GmbH [DSMZ], Braunschweig, Germany). On the day previous to each experiment, one colony of *P. aeruginosa* originally isolated in Tryptone-Soya-Broth (TSA, Oxoid, Wesel) is seeded into 50 ml media and grown for approximately 20 hours at 37° C. with agitation. On the day of the experiment, cells near the end of their exponential phase of growth are washed three times by centrifugation and resuspended in sterile distilled water. The titer of *P. aeruginosa* in the final working suspension ranges from 0.8 to 2.4x10 cfu/mL. PIXV strain BeAr 35645; Brazil 1961, ATCC #VR-371, is propagated in Baby Hamster Kidney cells (BHK cells, DSKZ-ACC 33, DMSZ, Braunschweig, Germany) at 37° C. in Eagle's Minimum Essential Medium (EMEM) available from Biochrom (Berlin, Germany), containing 10% FCS and 0.1% penicillin/streptomycin and harvested from infected cell monolayers at a concentration of $1.2\times10^{10}$ $TCID_{50}$/ml. VACV strain Elstree B5/Lister (WHO reference strain; Czerny and Mahnel, 1990) is grown in BHK cells at 37° C. in Eagle's Minimum Essential Medium (EMEM) containing 10% FCS and 0.1% penicillin/streptomycin and used at a $TCID_{50}$/mL ranging from $2\times10^{6}$ to $4\times10^{6}$.

Chemical disinfectants: Formaldehyde and guanidium thiocyanate are available from Roth GmbH (Karlsruhe, Germany), with the later being dissolved at a concentration of 7 M in sterile distilled water and its pH adjusted between 7 to 8 at room temperature with Tris-HCl. Peracetic acid and sodium hypochlorite containing 6.7% active chlorine as determined by iodometric determination are available from Sigma-Aldrich (Taufkirchen, Germany). Before use, the hypochlorite solution is adjusted to pH 7.5 with hydrochloric acid. Glutaraldehyde available from Sigma-Aldrich (Taufkirchen, Germany) is activated before each experiment by adjusting it to pH 9.3 with sodium bicarbonate. Hydrogen peroxide 30% is available from Merck-VWR International, Darmstadt, Germany. Cupric chloride dehydrate (>99% ACS reagent (Sigma-Aldrich, Taufkirchen, Germany)) and 0.003% hydrogen peroxide; with this last substance being added to assure instant liquid oxygenation for efficient free radical generation.

Microbial inactivation: A microbial suspension (typically 50 μl) containing either $1\times10^{8}$ spores$\times$mL$^{-1}$, 0.8 to $2.4\times10^{9}$ *P. aeruginosa* cells$\times$mL$^{-1}$, $1.2\times10^{10}$ PIXV Tissue Culture Infectious Dose 50 ($TCID_{50}$)$\times$mL$^{-1}$, or $4\times10^{6}$ VACV $TCID_{50}\times$mL$^{-1}$ is dispensed into 1.5 ml Eppendorf type tubes carefully avoiding microbial contamination of the inside walls of the tube above liquid level. An equal volume of either PBS as a control without inactivating effect or disinfectant at various concentrations is added and the mixture with microbes and disinfectant is incubated at 21° C. for 30 minutes with a 10 second initial mixing at 300 rpm (Eppendorf Thermomixer comfort, Eppendorf AG., Hamburg, Germany). Only cupric ascorbate is prepared in situ by adding to 50 μl of microbial suspension, 25 μl cupric chloride at 4-fold the intended final concentration, followed by 20 μl of ascorbic acid at 5×, and finally 5 μl of hydrogen peroxide at 20× the intended final concentration. After disinfectant treatment, nine volumes (900 μl) of either ice-cold Tryptone Soya Broth (TSB, Oxoid, Wesel, Germany) for bacteria or ice-cold EMEM with 10% fetal calf serum for viruses are added to the treatment mixes in order to slow down any remaining inactivation process. Surviving bacteria are analyzed in aliquots by serial dilution and titration onto TS agar plates. Viruses are serially diluted in EMEM supplemented with 5% fetal calf serum and in dilutions ranging from between $10^{-5}$ to $10^{-8}$ plated on to BHK cell monolayers in 96-well cell culture microtest plates. The medium is removed from cells, and the virus in the sample (25 μl) is adsorbed for one hour. The inoculum is removed and replaced with fresh EMEM with 10% FCS (25 μl per well) before the plates are incubated overnight at 37° C. in 4% $CO_2$ atmosphere. The amount of surviving virus is determined by the $TCID_{50}$ method on BHK cell monolayers. Other aliquots of the same exposed sample are tested by PCR and ELISA as described below.

DNA and RNA preparation: Nucleic acids, DNA, or RNA from VACV or PIXV, respectively, are extracted from a 100 μl aliquot of the sample inactivated with the studied disinfectants. Purification is performed by using either the QIAamp® DNA Mini Kit or the QIAamp® Viral RNA Mini Kit (Qiagen, Hilden, Germany) according to the manufacturer's instructions with minor modifications. Viral DNA and RNA are eluted with 100 μl of the cognate buffer. Generally, 1 μl of DNA is subjected to the VACV specific real-time PCR (rt-PCR) and 5 μl of the cognate buffer. Generally, 1 μl of DNA is subjected to the VACV specific real-time PCR (rtPCR) and 5 μl RNA is subjected to the PIXV specific real-time Reverse Transcriptase PCR (rtRT-PCR).

rtPCR and rtRT-PCR: For real-time PCR either the one-step RT-PCR, the HotStarTaq® system, or the TaqDNA Polymerase system from Qiagen GmbH or either ice-cold Tryptone Soya Broth (TSB, Oxoid, Wesel, Germany) for bacteria or (Hilden, Germany) chemistries are used with either TaqMan- or SYBR Green1 (TIB Molbiol GmbH, Berlin, Germany), respectively. The fluorescent reporter dye of the viral probe is a 6-carboxyfluorescent (FAM) located at the 5' end in all 5'-nuclease assays. The quencher, a 6-carboxy-tetramethyl-rhodamine (TAMRA), is located at the 3'end. Purified nucleic acids are used in viral PCR assays and extensively washed and resuspended spores or vegetative cell suspensions are directly applied to the respective PCR test. The rtPCR as well as the rtRT-PCR assays are performed in microtest plates (Biozym Scientific GmbH, Germany) in a final volume of either 25 μl or 20 μl on an Opticon™ device Type 1 (BioRad, Laboratories Inc., USA). Primer-, 5'-nuclease probe, SYBR Green I, $Mg^{++}$- and dNTP-concentrations are optimized by titration. Each real-time PCR and RT-PCR is performed in duplicates or triplicates and individual experiments are repeated two to four times. Negative controls contain water instead of a potential nucleic acid template. Impairment of disinfectants on either PCR or RT PCR tests are correlated to the $C_1$ (Cycle threshold), which corresponds to the first cycle number in which the fluorescence signal significantly increases from the baseline and background.

Enzyme-linked immunoassay (ELISA): All ELISAs are performed in 96 microwell plates (Maxisorb™, Thermo Fisher Scientific, Dreieich, Germany) that are coated with 3 to 4 μg antibody per well either by incubation over night at 4° C. or by incubation for two hours at 37° C. while plates for viral ELISAs are washed and blocked with 1% FCS in PBS-T (PBS plus 0.01% Tween 20) for I hour at room temperature (RT). Plates for bacterial ELISAs are blocked with 1% low-fat-milk powder in PBS for 30 minutes at RT. In addition, plates for viral ELISA are overlayed with liquid plate sealer (Candor Bioscience GmbH, Wangen, Germany) and are used for ELISA studies within three to four weeks. Plates for bacterial ELISAs are used and freshly coated each time.

For the detection of PIXV, the species specific monoclonal antibody PixcT 6/2 are used (available from the University of Veterinary Medicine, Hannover, Germany) as the capture antibody. For the detection of VACV, an equimolar mixture of the monoclonal antibodies mAB 5B1 and 5B4 can be used. *P. aeruginosa* and *B. atrophaeus* endospores are captured with specific rabbit polyclonal (pAb) antibodies produced in a laboratory setting. Antigen incubation is performed for either one or two hours at room temperature (21° C.) or at 37° C. Bound viral and bacterial antigens are detected by using either biotinylated species specific monoclonal (mAb), WIS pAb anti-*P. aeruginosa* 1:400) and after extensive washing the conjugate Streptavidin-horseradish peroxidase (PSA, available from GE Healthcare, USA) is added to the wells diluted 1:6000 in PBS-FT. Plates are incubated for 30 min at 21° C. with agitation and after three washes with PBS-T, staining is performed with the colorimetric substrate 3-3',5,5'-tetramethylbenzidine (TMB, available from Serva, Heidelberg, Germany) for 10 minutes. Furthermore, color development is stopped with 2 M sulphuric acid and absorbance is measured at 450 nm. Improvement of ELISA results obtained after cupric ascorbate disinfection is evaluated by the addition of EDTA, (pH 8, in a final concentration of 2, 10, 20, 40, and 100 mM). The enhancement of ELISA results after peracetic acid can be attempted by the addition of either 1 M Tris, pH 8, or catalase in a final concentration ranging from 32 to 324 units). All three potential ELISA enhancers (EDTA, Tris, and catalase) are available from Sigma Aldrich, Germany and are added to samples after the 30 min inactivation with disinfectants.

Figure 6A:
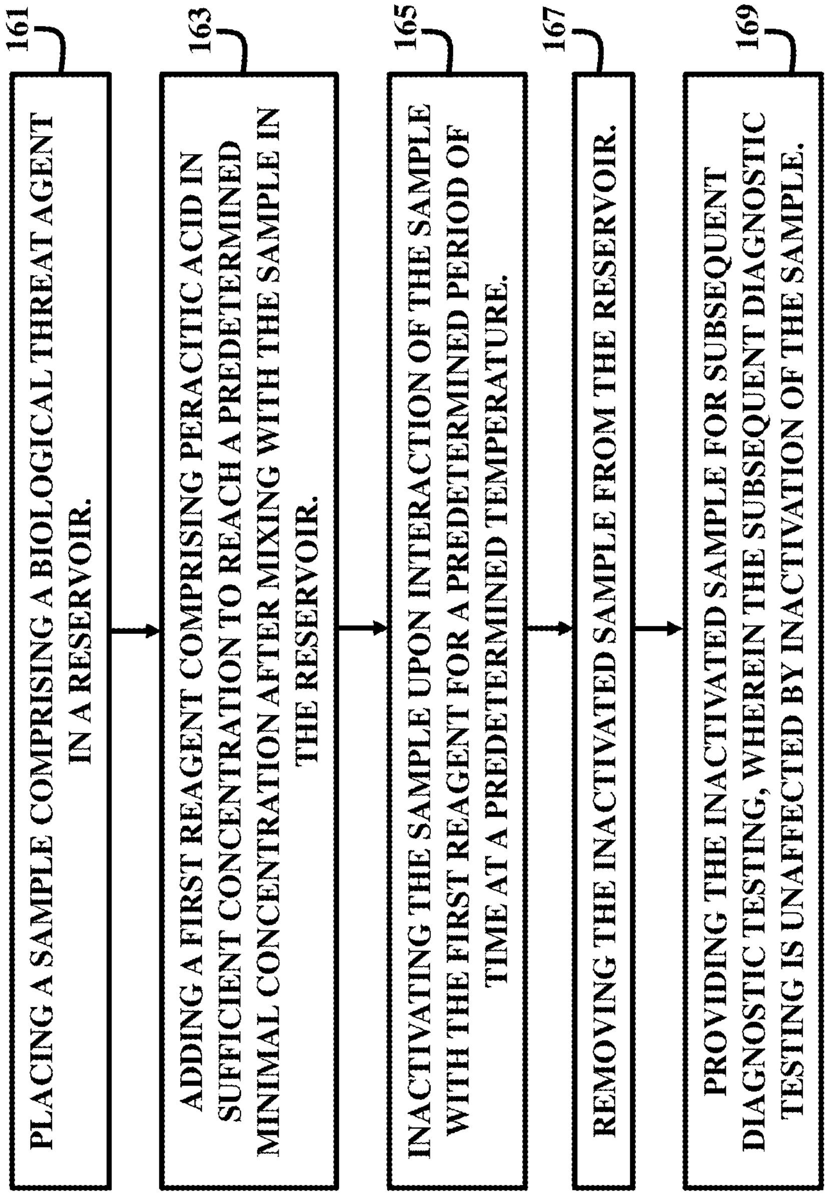
FIGS. 6A and 6B are flow diagrams illustrating methods according to the embodiments herein.

FIG. 6A, with reference to FIGS. 1 through 5B, is a flow diagram illustrating a method of processing biological threat agents, whereby the method comprises placing (161) a sample comprising a biological threat agent in a reservoir 52; adding (163) a first reagent comprising peracetic acid in sufficient concentration to reach a predetermined minimal concentration after mixing with the sample in the reservoir 52; inactivating (165) the sample upon interaction of the sample with the first reagent for a predetermined period of time at a predetermined temperature; removing (167) the inactivated sample from the reservoir 52; and providing (169) the inactivated sample for subsequent diagnostic testing, wherein the subsequent diagnostic testing is unaffected by inactivation of the sample. The peracetic acid in the reservoir 52 should be in sufficient concentration so as to reach, after mixing with the sample, a minimal concentration of 0.03% v/v. For example a tested effective mixture includes placing peracetic acid of 0.06% v/v in the reservoir 52 to which an equal volume of the sample is added, resulting in an active final concentration of 0.03% v/v. The sample and the first reagent may be placed in the reservoir 52 for approximately 30 minutes at approximately 21° C. The method may further comprise adding a second reagent comprising any of diluents and catalase in the reservoir 52 to decompose any remaining peracetic acid after inactivation. The subsequent diagnostic testing may comprise any of a polymerase chain reaction test and an enzyme linked immunoassays test. The peracetic acid preferably comprises 0.03% peracetic acid as a final active concentration after diluting with the sample.

Figure 6B:
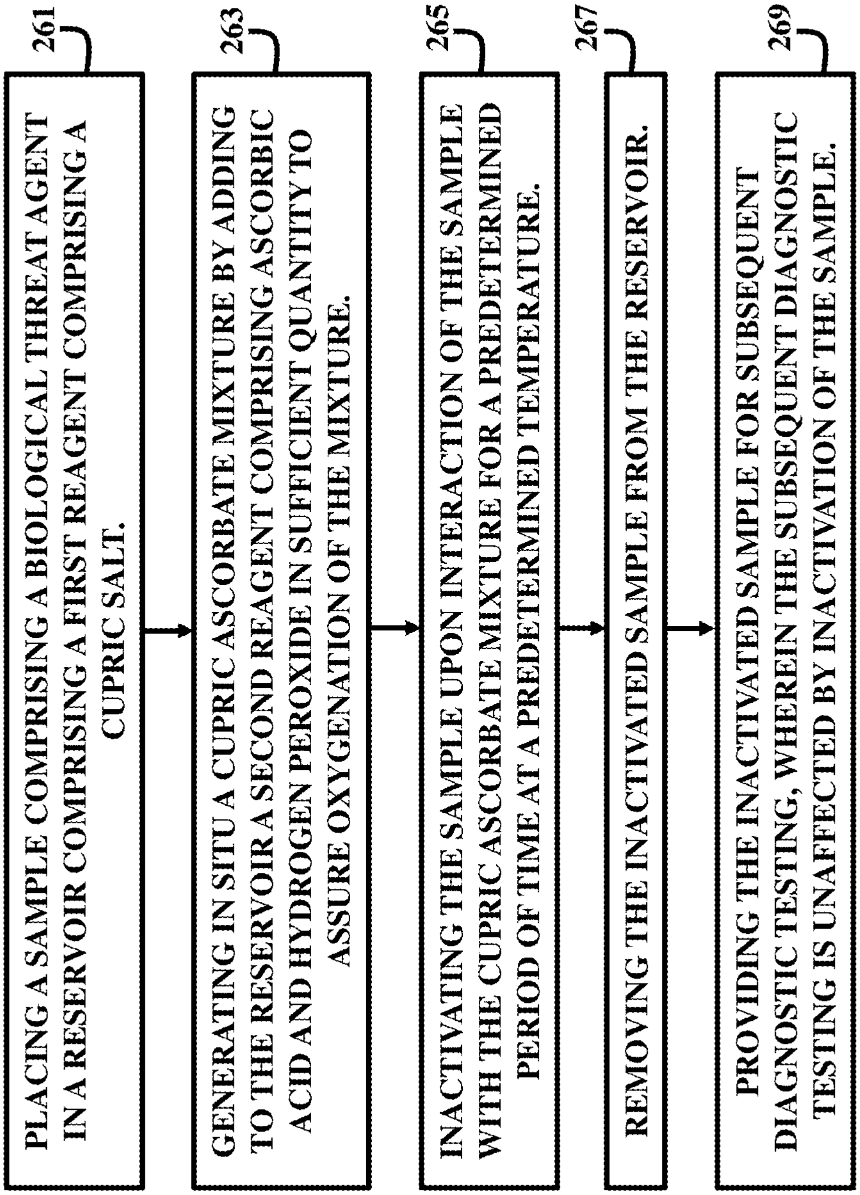

FIG. 6B, with reference to FIGS. 1 through 6A, is a flow diagram illustrating another method of processing biological threat agents, whereby the method comprises placing (261) a sample comprising a biological threat agent in a reservoir 52 comprising a first reagent comprising a cupric salt; generating (263) in situ a cupric ascorbate mixture by adding to the reservoir 52 a second reagent comprising ascorbic acid and an amount of hydrogen peroxide that is in sufficient quantity to assure oxygenation of the mixture; inactivating (265) the sample upon interaction of the sample with the cupric ascorbate mixture for a predetermined period of time at a predetermined temperature; removing (267) the inactivated sample from the reservoir 52; and providing (269) the inactivated sample for subsequent diagnostic testing, wherein the subsequent diagnostic testing is unaffected by inactivation of the sample. The sample with the first reagent and the second reagent may be placed in the reservoir 52 for approximately 30 minutes at approximately 21° C. The subsequent diagnostic testing may comprise any of a polymerase chain reaction test, nucleic acid hybridization, other nucleic acid-based tests, an enzyme linked immunoassay, immunoprecipitation, and any other immuno-based tests. The cupric salt may comprise any of cupric chloride and sulfate. The first reagent preferably comprises the cupric salt in a sufficient concentration so as to result in a final concentration of 0.5% w/v in cupric ions after dilution with the sample and the second reagent. The method may further comprise adding ethylenediaminetetraacetic acid to the inactivated sample.

The high risk associated with biologically threat agents determines that any suspicious sample should be handled under strict surety and safety controls and processed under high level containment in specialized laboratories. Accordingly, the embodiments herein provide a rapid, reliable, and simply method and device for the complete inactivation of a wide range of pathogens including spores, vegetative bacteria, and viruses, while preserving microbial nucleic acid fragments suitable for PCR reactions and other nucleic acid-based methods and proteinaceous epitopes for the detection by ELISA or other immunoassays. Conventional methods and devices for providing disinfectants either do not inactivate completely high titers of bacterial spores or viruses, or show high microbicidal activity but obliterate future PCR or ELISA diagnostic testing to detect bacterial spores or viruses. Among all the formulations experimentally tested, only high level inactivation (more than 6 $\log_{10}$) of bacterial spores (*B. atrophaeus*), vegetative bacteria (*P. aeruginosa*), an RNA-virus (the Alphavirus PIXV), or a DNA-virus (the Orthopoxvirus VACV) is attained within 30 minutes at 21° C. by treatment with either peracetic acid or cupric ascorbate with minimal hindrance of subsequent PCR tests and immunoassays. The method and device provided by the embodiments herein enable quick rendering of field samples of biological agents and permit further analysis under lower containment and at a lower cost than conventional solutions.

Accordingly, the embodiments herein provide liquid reagents with high efficiency to inactivate microbial organisms and viruses that simultaneously preserve the high sensitivity of subsequent diagnostics performed at a lower level of containment and cost. The identified reagents are integrated into a self-contained device for inactivation of microbes in environmental samples for subsequent detection and diagnostics.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A hand-held device for sample preparation of samples suspected of containing biological threat agents, said device comprising:

a reservoir for holding a sample suspected of containing a biological threat agent;

a first dispensing unit containing a first reagent comprising peracetic acid and operatively connected to said reservoir, wherein said first dispensing unit adds said peracetic acid in sufficient concentration to reach a predetermined minimal concentration after mixing with said sample in said reservoir, wherein said sample becomes inactivated upon interaction of said sample with said first reagent for a predetermined period of time at a predetermined temperature; and a filter operatively connected to said reservoir and said first dispensing unit, wherein said filter filters the inactivated sample as it is removed from said reservoir, wherein said inactivated sample is capable of subsequent diagnostic testing, and wherein said subsequent diagnostic testing comprises immune or genetic-based testing used to detect or identify the biological threat agent and which is unaffected by inactivation of the sample.

2. The device of claim 1, wherein said peracetic acid in said reservoir is in sufficient concentration so as to reach a minimal concentration of 0.03% v/v after mixing with said sample.

3. The device of claim 1, wherein said sample and said first reagent are placed in said reservoir for approximately 30 minutes at approximately 21° C.

4. The device of claim 1, further comprising a second dispensing unit operatively connected to said reservoir, wherein said second dispensing unit adds a second reagent comprising any of diluents and catalase to said reservoir to decompose any remaining peracetic acid after inactivation.

5. The device of claim 1, wherein said subsequent diagnostic testing comprises any of a polymerase chain reaction test and an enzyme linked immunoassays test.

6. The device of claim 1, wherein said peracetic acid comprises 0.03% peracetic acid as a final active concentration after diluting with said sample.

7. The device of claim 1, wherein said first reagent comprises cupric salt in a sufficient concentration so as to result in a final concentration of 0.5% w/v in cupric ions.

8. The device of claim 7, further comprising a second dispensing unit operatively connected to said reservoir, wherein said second dispensing unit adds a second reagent comprising ascorbic acid and an amount of hydrogen peroxide to said reservoir to generate a cupric ascorbate mixture, wherein said amount of hydrogen peroxide is in sufficient quantity to assure oxygenation of said mixture.

* * * * *